(12) United States Patent
Jang (10) Patent No.: US 6,200,334 B1
(45) Date of Patent: *Mar. 13, 2001

(54) TUBULAR STENT CONSISTS OF NON-PARALLEL EXPANSION STRUTS AND CONTRALATERALLY ATTACHED DIAGONAL CONNECTORS

(76) Inventor: G. David Jang, 30725 Eastburn La., Redlands, CA (US) 92374

(*) Notice: Subject to any disclaimer, the term of this patent is extended or adjusted under 35 U.S.C. 154(b) by 0 days.

This patent is subject to a terminal disclaimer.

(21) Appl. No.: 09/243,911

(22) Filed: Feb. 3, 1999

Related U.S. Application Data
(60) Provisional application No. 60/073,509, filed on Feb. 3, 1998.

(51) Int. Cl.[7] ................................................. A61F 2/06
(52) U.S. Cl. ............................. 623/1.1; 623/12; 606/198
(58) Field of Search .............................. 623/1.1, 1.14, 623/1.11, 1.15, 12; 606/198

(56) References Cited

U.S. PATENT DOCUMENTS 5,945,743 * 9/1999 Jang ........................................... 623/1
5,948,016 * 9/1999 Jang ........................................... 623/1

FOREIGN PATENT DOCUMENTS 297 02 671 U 5/1997 (DE).
WO 97/32543 9/1997 (WO).
WO 99/01088 1/1999 (WO).
WO 99/15107 4/1999 (WO).

* cited by examiner

Primary Examiner—Michael Buiz
Assistant Examiner—Anthony S. King
(74) Attorney, Agent, or Firm—Van Mahamedi; Wilson Sonsini Goodrich & Rosati (57) ABSTRACT

An intra-luminal vascular stent in a non-expanded state with a longitudinal axis, comprises a plurality of expansion strut pairs forming a first expansion column. Each expansion strut pair includes a stair-step expansion strut, a straight-line expansion strut and a joining strut coupling an end of the strut pair, which forms cell slot. Each of the expansion strut pair has three longitudinal axes that are aligned in a non-parallel relationship to the stent longitudinal axis. A plurality of expansion strut pairs forms a second expansion column. Each expansion strut pair includes a straight-line expansion strut, a stair-step expansion strut and a joining strut coupling an end of the strut pair, which forms a cell slot. Each of the expansion strut pair has three longitudinal axes that are aligned in a non-parallel relationship to the stent longitudinal axis. A plurality of serial connecting struts forms a first serial connecting strut column and includes a first serial connecting strut. The first serial connecting strut column couples the first expansion column to the second expansion column.

61 Claims, 4 Drawing Sheets

TUBULAR STENT CONSISTS OF NON-PARALLEL EXPANSION STRUTS AND CONTRALATERALLY ATTACHED DIAGONAL CONNECTORS

This application claims benefit to U.S. provisional 60/073,509 filed Feb. 3, 1998.

BACKGROUND OF THE INVENTION

1. Field of the Invention

This invention relates to intravascular stents, and more particularly to an intravascular stent, which provides easy introduction through tortuous sections of vessels but this invention can be used as an intraluminal-scaffolding device in any tubular body anatomy.

2. Description of the Related Art

Angioplasty, either coronary or general vessel, has advanced to become the most effective means for revascularization of stenosed vessels. In the early 1980's, angioplasty first became available for clinical practice in the coronary artery, and has since proven an effective alternative to conventional bypass graft surgery. Balloon catheter dependent angioplasty has consistently proven to be the most reliable and practical interventional procedure. Other ancillary technologies such as laser based treatment, or directional or rotational atherectomy, have proven to be either of limited effectiveness or dependent on balloon angioplasty for completion of the intended procedure. Restenosis following balloon-based angioplasty is the most serious drawback and is especially prevalent in the coronary artery system.

Many regimens have been designed to combat restenosis, with limited success, including laser based treatment and directional or rotational atherectomy. Intravascular stenting, however, noticeably reduces the restenosis rate following angioplasty procedures. The procedure for intravascular stent placement typically involves pre-dilation of the target vessel using balloon angioplasty, followed by deployment of the stent, and expansion of the stent such that the dilated vessel walls are supported from the inside.

The intravascular stent functions as scaffolding for the lumen of a vessel. The scaffolding of the vessel walls by the stent serve to: (a) prevent elastic recoil of the dilated vessel wall, (b) eliminate residual stenosis of the vessel; a common occurrence in balloon angioplasty procedures, (c) maintain the diameter of the stented vessel segment slightly larger than the native unobstructed vessel segments proximal and distal the stented segment and (d) as indicated by the latest clinical data, lower the restenosis rate. Following an angioplasty procedure, the restenosis rate of stented vessels has proven significantly lower than for not stented or otherwise treated vessels; treatments include drug therapy and other methods mentioned previously.

Another benefit of vessel stenting is the potential reduction of emergency bypass surgery arising from angioplasty procedures. Stenting has proven to be effective in some cases for treating impending closure of a vessel during angioplasty. Stenting can also control and stabilize an unstable local intimal tear of a vessel caused by normal conduct during an angioplasty procedure. In some cases, an incomplete or less than optimal dilatation of a vessel lesion with balloon angioplasty can successfully be opened up with a stent implant.

Early in its development, the practice of stenting, especially in coronary arteries, had serious anticoagulation problems. However, anticoagulation techniques have since been developed and are becoming simpler and more effective. Better and easier to use regimens are continuously being introduced, including simple outpatient anticoagulation treatments, resulting in reduced hospital stays for stent patients.

An example of a conventional stent patent is U.S. Pat. No. 5,102,417 (hereafter the Palmaz Patent). The stent described in the Palmaz Patent consists of a series of elongated tubular members having a plurality of slots disposed substantially parallel to the longitudinal axis of the tubular members. The tubular members are connected by at least one flexible connector member.

The unexpanded tubular members of the Palmaz Patent are overly rigid so that practical application is limited to short lengths. Even with implementation of the Multi-link design with flexible connector members connecting a series of tubular members, longer stents can not navigate tortuous blood vessels. Furthermore, the rigidity of the unexpanded stent increases the risk of damaging vessels during insertion. Foreshortening of the stent during insertion complicates accurate placement of the stent and reduces the area that can be covered by the expanded stent. There is, further, no method of programming the stent diameter along its longitudinal axis to achieve a tapered expanded stent, and no method of re-enforcement of stent ends or other regions is provided for.

Another example of a conventional stent patent is WO 96/03092, the Brun patent. The stent described in the Brun patent is formed of a tube having a patterned shape, which has first and second meander patterns. The even and odd first meander patterns are 180 degrees out of phase, with the odd patterns occurring between every two even patterns. The second meander patterns run perpendicular to the first meander patterns, along the axis of the tube.

Adjacent first meander patterns are connected by second meander patterns to form a generally uniform distributed pattern. The symmetrical arrangement with first and second meander patterns having sharp right-angle bends allows for catching and snagging on the vessel wall during delivery. Furthermore, the large convolutions in the second meander pattern are not fully straightened out during expansion reducing rigidity and structural strength of the expanded stent. There is, further, no method of programming the stent diameter along its longitudinal axis to achieve a tapering stent design, and no method of re-enforcement of stent ends or other regions is provided for.

These and other conventional stent designs suffer in varying degrees from a variety of drawbacks including: (a) inability to negotiate tortuous bends in vessels due to columnar rigidity of the unexpanded stent; (b) lack of structural strength, radial & axio-lateral, of the expanded stent; (c) significant foreshortening of the stent during expansion; (d) limited stent length; (e) parallel expanded stent diameter in long stent; (f) poor crimping characteristics; and (g) rough surface modulation of the unexpanded stent.

There is a need for a stent with sufficient longitudinal flexibility in the unexpanded state to allow for navigation through tortuous vessels. There is a further need for a stent that is structurally strong in the unexpanded state such that risk of damage or distortion during delivery is minimal. A further need exists for a stent that maintains substantially the same longitudinal length during expansion to allow greater coverage at the target site and simplify proper placement of the stent. Yet a further need exists for a stent design with sufficient longitudinal flexibility that long stents of up to 100 mm can be safely delivered through tortuous vessels. There is a need for a stent that is configured to expand to variable diameters along its length, such that a taper can be achieved in the expanded stent to match the natural taper of the target vessel. A need exists for a stent which; (i) can be crimped tightly on the expansion balloon while maintaining a low profile and flexibility, (ii) has a smooth surface modulation when crimped over a delivery balloon, to prevent catching and snagging of the stent on the vessel wall during delivery or (iii) with enhanced expansion rings of the stent securely positioned against the vessel walls of the target blood vessel.

SUMMARY OF THE INVENTION

Accordingly an object of the present invention is to provide a scaffold for an interior lumen of a vessel.

Another object of the invention is to provide a stent, which prevents elastic recoil of the vessel following angioplasty.

A further object of the invention is to provide a stent that maintains a larger vessel lumen compared to the results obtained only with balloon angioplasty.

Yet another object of the invention is to provide a stent of negligible foreshortening of a stent length when expanded.

Another object of the invention is to provide a stent with increased flexibility when delivered to a selected site in a vessel.

A further object of the invention is to provide a stent with a low profile when crimped over a delivery balloon of a stent assembly.

Yet a further object of the invention is to provide a stent with reduced tuliping of a stent frame.

Another object of the invention is to provide a chain mesh stent that reduces vessel "hang up" in a tortuous vessel or a vessel with curvature.

A further object of the invention is to provide a chain mesh stent that increases radial and axio-lateral strength of the expanded stent.

These and other objectives of the invention are achieved in a stent described in a non-expanded state. The stent of present invention is a 3-dimensional object with a generally tubular geometry, which includes inner and outer surface, inner and outer diameters, an internal tubular lumen, a wall thickness, a certain number of cells and a prescribed length. To describe the design geometry of the stent of present invention a cut-open 2-dimensional illustrations are used extensively in this provisional application. The 2-dimensional illustrations are laid out with the longitudinal axis of the stent horizontally aligned. Although the description of strut configurations of the stent of present invention is according to 2-dimensional and cut open drawings, the real stent of present invention is a 3-dimensional tubular object designed to function as a scaffolding device when expanded inside a blood vessel or an anatomic tubular structure of any kind in the body in which the stent can be implanted.

A first expansion column includes of a plurality of first expansion strut pairs of a generally non-horizontal arrangement and with the long axis of first expansion strut pairs aligned at a diagonal angle to the horizontal longitudinal axis of a tubular stent in the 2-dimensional drawings. A diagonal angle of the longitudinal axes of first expansion strut pairs point toward one direction, different from a respective angle in second expansion column. The diagonal angle of a non-horizontal expansion strut pairs can be as little as 2–3 degrees or as high as 45–60 degrees from the horizontal plane of a tubular stent. However, the preferred diagonal angle of first expansion strut pairs is somewhere between 7–25 degrees. The longitudinal axes of a first and second expansion strut in a first expansion strut pair in a first expansion column are generally parallel to each other. However, the longitudinal axes of a first and second expansion strut in a first expansion strut pair can generally be non-parallel to each other. Variations of the diagonal angle of a non-horizontal expansion strut pair are within the scope of a tubular stent of present invention. Both parallel alignment and non-parallel alignment of a first and a second expansion strut of first expansion strut pairs is within the scope of a tubular stent of present invention.

A first expansion strut pair in first expansion column includes a first expansion strut of a stair-step configuration that is non-horizontal adjacent to a second expansion strut of a straight-line configuration that is non-horizontal. A first joining strut couples the first and second expansion struts making a closed loop at a proximal end of a first expansion strut pair. A second expansion strut pair includes a third expansion strut of a stair-step configuration that is non-horizontal adjacent to a second expansion strut of a straight-line configuration that is non-horizontal to a longitudinal axis of the tubular stent. A second joining strut couples a second and a third expansion strut making a closed loop at a distal end of a second expansion strut pair. A third expansion strut pair includes a fourth expansion strut of a straight-line configuration that is non-horizontal adjacent to a third expansion strut of a stair-step configuration that is non-horizontal. A third joining strut couples a third and a fourth expansion strut making a closed loop at a proximal end of a third expansion strut pair. A fourth expansion strut pair includes a fifth expansion strut of a stair-step configuration that is non-horizontal adjacent to a fourth expansion strut of a straight-line configuration that is non-horizontal. A fourth joining strut couples the fourth and fifth expansion struts making a closed loop at a distal end of a fourth expansion strut pair. A fifth expansion strut pair includes a sixth expansion strut of a straight-line configuration that is non-horizontal adjacent to a fifth expansion strut of a stair-step configuration that is non-horizontal. A fifth joining strut couples the fifth and sixth expansion struts making a closed loop at a proximal end of a fifth expansion strut pair. A sixth expansion strut pair includes a seventh expansion strut of a stair-step configuration that is non-horizontal adjacent to a sixth expansion strut of a straight-line configuration that is non-horizontal. A sixth joining strut couples the sixth and seventh expansion struts making a closed loop at a distal end of a sixth expansion strut pair. A seventh expansion strut pair includes an eight expansion strut of a straight-line configuration that is non-horizontal adjacent to a seventh expansion strut of a stair-step configuration that is non-horizontal. A seventh joining strut couples the seventh and eighth expansion struts making a closed loop at a proximal end of a seventh expansion strut pair. In the illustrations in this provisional application, there are 12 first expansion strut pairs arranged in an alternating and unbroken chain in a first expansion column.

An expansion strut pair includes two companion expansion struts and a joining strut to form a closed or blind loop at a proximal or distal end. This expansion strut pair loop construction can be repeated to make the prescribed number of expansion strut pairs around the circumference in an unbroken fashion in a first expansion column of a tubular stent of present invention. A set of two consecutive closed loop expansion strut pairs in an unbroken chain in an expansion column is called expansion strut pair cycles. In this provisional application, the illustrations would contain 12 expansion strut pairs making 6 expansion strut pair cycles in a first expansion column in the cut-open 2-dimensional drawings. Each expansion strut pair cycle would have one closed loop pointing proximally and one closed loop pointing distally. Of the 12 expansion strut pairs in a first expansion column, therefor, one half of expansion strut pair closed loops point proximally and one half of expansion strut pair closed loops point distally. Although there are six (6) expansion strut pair cycles in the main illustrations of this provisional application, the number of expansion strut pairs can variably be changed according to a prescribed requirement of a specific stent made. This variability of having a more or less than twelve expansion strut pairs in an expansion column is within the scope of a tubular stent of present invention.

In a first expansion column, each expansion strut pair consists of one straight-line strut, one stair-step strut and a joining strut to make a closed loop strut pair. However, each expansion strut pair can be made of two straight-line expansion struts or of two stair-step expansion struts. These mixing variation of expansion strut pair configuration of stair-step or straight-line is within the scope of a tubular stent of present invention.

A first expansion strut pair first corner is formed where the first joining strut is coupled to the first expansion strut, and a first expansion strut pair second corner is formed where the first joining strut is coupled to the second expansion strut. A second expansion strut pair first corner is formed where the second joining strut is coupled to the second expansion strut, and a second expansion strut pair second corner is formed where the second joining strut is coupled to the third expansion strut. A third expansion strut pair first corner is formed where the third joining strut is coupled to the third expansion strut, and a third expansion strut pair second corner is formed where the third joining strut is coupled to the fourth expansion strut. A fourth expansion strut pair first corner is formed where the fourth joining strut is coupled to the fourth expansion strut, and a fourth expansion strut pair second corner is formed where the fourth joining strut is coupled to the fifth expansion strut. All the expansion strut pairs in a first expansion column are joined with their respective joining struts forming a first and second corner on each expansion strut pair closed loop.

A second expansion column includes of a plurality of second expansion strut pairs of a generally non-horizontal arrangement and with the long axis of second expansion strut pairs aligned at a diagonal angle to the horizontal longitudinal axis of a tubular stent in the 2-dimensional drawings in this provisional application. A diagonal angle of the longitudinal axes of second expansion strut pairs point toward another direction, different from a respective diagonal angle in first expansion column. The diagonal angle of a non-horizontal expansion strut pairs can be as little as 2–3 degrees or as high as 45–60 degrees from the horizontal plane of a tubular stent. However, the preferred diagonal angle of second expansion strut pairs is somewhere between 7–25 degrees. The longitudinal axes of first and second expansion struts in a second expansion strut pair of second expansion column are generally parallel to each other. However, the longitudinal axes of first and second expansion struts in a second expansion strut pair can generally be non-parallel to each other. Variations of the diagonal angle of a non-horizontal expansion strut pair are within the scope of a tubular stent of present invention. Both parallel alignment and non-parallel alignment of first and second expansion strut of second expansion strut pairs is also within the scope of a tubular stent of present invention.

The diagonal angle of second expansion strut pairs in a second expansion column is different form the diagonal angle of first expansion strut pairs in a first expansion column. The underside of second expansion strut pairs in a second expansion column and first expansion strut pairs in a first expansion column face to each because the apposing expansion strut pairs in a second and first expansion column have opposing diagonal angles in similar degree upward. due to an opposing diagonal angles of the respective apposing expansion strut pairs in a similar degree of angulation. However, a diagonal angle of second expansion strut pairs in a second expansion column can have a similar diagonal angle in a similar direction as a diagonal angle of first expansion strut pairs in a first expansion column, so that the diagonal angles of second expansion strut pairs in second expansion column and first expansion strut pairs of first expansion column could parallel to each other. Similarly, while the two diagonal angles of expansion strut pairs in the two adjacent expansion columns may point to the similar direction, they do not have to parallel to each other. These variations of arranging the diagonally angled expansion strut pairs in two adjacent expansion columns to make different permutations of stent strut pattern are within the scope of a tubular stent of present invention.

A first expansion strut pair in a second expansion column includes a first expansion strut of a stair-step configuration that is non-horizontal adjacent to a second expansion strut of a straight-line configuration that is non-horizontal. A first joining strut couples the first and second expansion struts making a closed loop at a distal end of a first expansion strut pair. A second expansion strut pair includes a third expansion strut of a stair-step configuration that is non-horizontal adjacent to a second expansion strut of a straight-line configuration that is non-horizontal. A second joining strut couples the second and third expansion struts making a closed loop at a proximal end of a second expansion strut pair. A third expansion strut pair includes a fourth expansion strut of a straight-line configuration that is non-horizontal adjacent to a third expansion strut of a stair-step configuration that is non-horizontal. A third joining strut couples the third and fourth expansion struts making a closed loop at a distal end of a third expansion strut pair. A fourth expansion strut pair includes a fifth expansion strut of a stair-step configuration that is non-horizontal adjacent to a fourth expansion strut of a straight-line configuration that is non-horizontal. A fourth joining strut couples the fourth and fifth expansion struts making a closed loop at a proximal end of a fourth expansion strut pair. A fifth expansion strut pair includes a sixth expansion strut of a straight-line configuration that is non-horizontal adjacent to a fifth expansion strut of a stair-step configuration that is non-horizontal. A fifth joining strut couples the fifth and sixth expansion struts making a closed loop at a distal end of a fifth expansion strut pair. A sixth expansion strut pair includes a seventh expansion strut of a stair-step configuration that is non-horizontal adjacent to a sixth expansion strut of a straight-line configuration that is non-horizontal. A sixth joining strut couples the sixth and seventh expansion struts making a closed loop at a proximal end of a sixth expansion strut pair. A seventh expansion strut pair includes an eighth expansion strut of a straight-line configuration that is non-horizontal adjacent to a seventh expansion strut of a stair-step configuration that is non-horizontal. A seventh joining strut couples the seventh and eighth expansion struts making a closed loop at a distal end of a seventh expansion strut pair. In the illustrations in this provisional application, there are 12 first expansion strut pairs arranged in an unbroken chain in a second expansion column.

An expansion strut pair includes two companion expansion struts and a joining strut to form a closed or blind loop at a proximal or distal end. This expansion strut pair loop construction can be repeated to make the prescribed number of expansion strut pairs around the circumference in an unbroken fashion in a second expansion column of a tubular stent of present invention. A set of two consecutive closed loop expansion strut pairs in an unbroken chain in an expansion column is called expansion strut pair cycles. In this provisional application, the illustrations would contain 12 expansion strut pairs making 6 expansion strut pair cycles in a second expansion column in the cut-open 2-dimensional drawings. Each expansion strut pair cycle would have one closed loop pointing proximally and one closed loop pointing distally. Of the 12 expansion strut pairs in a first expansion column, therefor, one half of expansion strut pair closed loops point proximally and one half of expansion strut pair closed loops point distally. Although there are six (6) expansion strut pair cycles in the main illustrations of this provisional application, the number of expansion strut pair cycles can variably be changed according to a prescribed requirement of a specific stent made. This variability of having a more or less than twelve expansion strut pairs in an expansion column is within the scope of a tubular stent of present invention.

A first connecting strut column is formed of a plurality of first connecting struts. A first connecting strut in a first connecting strut column includes a connecting strut proximal section, a connecting strut distal section and a connecting strut intermediate section. A first connecting strut proximal section has two parts: a short part and a long part. A first connecting strut proximal section short part is coupled at a perpendicular or slant angle to the contralateral out side of a distal end of a second expansion strut of a second expansion strut pair in a first expansion column. A first connecting strut proximal section long part is coupled to the short part proximally at a generally perpendicular or a slant angle and to the intermediate section distally at a generally perpendicular or a slant angle. The proximal section long part generally parallels to the longitudinal axis of a second expansion strut of a second expansion strut pair in a first expansion column. However, the proximal section long part can be made not to parallel to a longitudinal axis of a second expansion strut of a second expansion strut pair in a first expansion column. A first connecting strut distal section has two parts: a short part and a long part. A first connecting strut distal section short part is coupled at a perpendicular or slant angle to the contralateral out side of a proximal end of a third expansion strut of a second expansion strut pair in a second expansion column. A first connecting strut distal section long part is coupled to the short part distally at a generally perpendicular or a slant angle and to the intermediate section proximally at a generally perpendicular or a slant angle. A distal section long part generally do not parallel to a longitudinal axis of a third expansion strut of a second expansion strut pair in a second expansion column. However, a distal section long part can be made to parallel to a longitudinal axis of a third expansion strut of a second expansion strut pair in a second expansion column. Th proximal and distal end of a first connecting strut point generally to opposite or different directions. A first connecting strut intermediate section proximal end is coupled at a slant angle to a first connecting strut proximal section long part and a first connecting strut intermediate section distal end is coupled at a slant angle to a first connecting strut distal section long part. The intermediate section of a first connecting strut traverses diagonally through the inter-connecting space separating a second expansion strut pair loop in a first expansion strut column and a second expansion strut pair loop in a second expansion strut column. There is a slight angulation at the center of a first connecting strut intermediate section in a tubular stent illustrated in main figures of this provisional application. However, the intermediate section of a first connecting strut can have a straight-line or all together different configuration as long as this intermediate section serves as a diagonally coupling role between first connecting strut proximal section and first connecting strut distal section, that are attached to contralateral sides on the apposed expansion strut pair loops. Furthermore, a first (diagonal) connector strut in a first connecting strut column that connects the contralateral sides of two opposing expansion strut pair loops in respective two adjacent expansion columns can have a variety of different configurations. One such shape is an "S-shape" first connecting strut adapted to diagonally link the contralateral sides on two apposing expansion strut pair loops. These varied potential shape modifications of a first connecting strut in a first connecting strut column is within the scope of a tubular stent of present invention.

A second, third, through sixth connecting strut in a first connecting strut column has identical connecting strut configuration like a first connecting strut in a first connecting strut column as described in the foregoing paragraph. A second, third through sixth connecting strut in a first connecting column connects a first expansion column to a second expansion column at their respective contralateral coupling locations to make a full and unbroken ring of connecting column around the circumference of a tubular stent of the present invention. A second connecting strut, in a similar manner as a first connecting strut described above, connects a fourth expansion strut pair loop in a first expansion column to a fourth expansion strut pair loop in a second expansion column. A third connecting strut connects a sixth expansion strut pair loop in a first expansion column to a sixth expansion strut pair loop in a second expansion column. A fourth connecting strut connects an eighth expansion strut pair loop in a first expansion column to an eighth expansion strut pair loop in a second expansion column. Likewise, a fifth connecting strut and a sixth connecting strut connects the tenth expansion strut pair loops and the twelfth expansion strut pair loops, respectively.

Other form or shape of a connector, beside the diagonal connector described in this application, configured to attach to the contralateral sides on apposing expansion strut pair loops can be used to couple a first and second expansion columns of non-parallel arrangement. The variation of any connector configuration contralaterally connecting two apposing expansion strut pair loops in two adjacent expansion columns of non-parallel arrangement is within the scope of a tubular stent of present invention.

A third expansion column includes of a plurality of third expansion strut pairs of a generally non-horizontal arrangement and with the long axis third expansion strut pairs in a third expansion column aligned at a diagonal angle to the horizontal longitudinal axis of a tubular stent in the 2-dimensional drawings in this provisional application. A diagonal angle arrangement of the longitudinal axes of third expansion strut pairs point toward different direction than a respective diagonal angle of the longitudinal axes of second expansion strut pairs in a second expansion column. The diagonal angle of a non-horizontal expansion strut pairs can be as little as 2–3 degrees or as high as 45–60 degrees from the horizontal plane of a tubular stent. However, the preferred diagonal angle of third expansion strut pairs is somewhere between 7–25 degrees. The longitudinal axes of first and second expansion struts in a first expansion strut pair in a third expansion column are generally parallel to each other. However, the longitudinal axes of first and second expansion struts in a first expansion strut pair can be non-parallel to each other. Variations of the diagonal angle of a non-horizontal expansion strut pair in an expansion column are within the scope of a tubular stent of present invention. Both parallel alignment and non-parallel alignment of first and second expansion strut of first expansion strut pairs in an expansion column is also within the scope of a tubular stent of present invention.

The diagonal angle of third expansion strut pairs in a third expansion column is different form the diagonal angle of second expansion strut pairs in a second expansion column. The upper sides of third expansion strut pairs in a third expansion column and second expansion strut pairs in a second expansion column face to each other because the apposing expansion strut pairs have opposing diagonal angles in similar degree downward. However, a diagonal angle of third expansion strut pairs in a third expansion column can have a similar diagonal angle in a similar direction as a diagonal angle of second expansion strut pairs in a second expansion column, so that the diagonal angles of third expansion strut pairs in third expansion column and second expansion strut pairs in a second expansion column would parallel to each other. Similarly, while the two diagonal angles of expansion strut pairs in the two adjacent expansion columns may point toward the similar direction, they do not have to parallel to each other. These variations of arranging the diagonally angled expansion strut pairs in two adjacent expansion columns to make different permutations of stent strut pattern are within the scope of a tubular stent of present invention.

A first expansion strut pair in third expansion column includes a first expansion strut of a stair-step configuration that is non-horizontal adjacent to a second expansion strut of a straight-line configuration that is non-horizontal. A first joining strut couples the first and second expansion struts making a closed loop at a distal end of the first expansion strut pair. A second expansion strut pair includes a third expansion strut of a stair-step configuration that is non-horizontal adjacent to a second expansion strut of a straight-line configuration that is non-horizontal. A second joining strut couples the second and third expansion struts making a closed loop at a proximal end of a second expansion strut pair. A third expansion strut pair includes a fourth expansion strut of a straight-line configuration that is non-horizontal adjacent to a third expansion strut of a stair-step configuration that is non-horizontal. A third joining strut couples the third and fourth expansion struts making a closed loop at a distal end of a third expansion strut pair. A fourth expansion strut pair includes a fifth expansion strut of a stair-step configuration that is non-horizontal adjacent to a fourth expansion strut of a straight-line configuration that is non-horizontal. A fourth joining strut couples the fourth and fifth expansion struts making a closed loop at a proximal end of a fourth expansion strut pair. A fifth expansion strut pair includes a sixth expansion strut of a straight-line configuration that is non-horizontal adjacent to a fifth expansion strut of a stair-step configuration that is non-horizontal. A fifth joining strut couples the fifth and sixth expansion struts making a closed loop at a distal end of a fifth expansion strut pair. A sixth expansion strut pair includes a seventh expansion strut of a stair-step configuration that is non-horizontal adjacent to a sixth expansion strut of a straight-line configuration that is non-horizontal. A sixth joining strut couples the sixth and seventh expansion struts making a closed loop at a proximal end of a sixth expansion strut pair. A seventh expansion strut pair includes an eighth expansion strut of a straight-line configuration that is non-horizontal adjacent to a seventh expansion strut of a stair-step configuration that is non-horizontal. A seventh joining strut couples the seventh and eighth expansion struts making a closed loop at a distal end of a seventh expansion strut pair. In the illustrations in this provisional application, there are 12 first expansion strut pairs arranged in an unbroken chain in a first expansion column.

An expansion strut pair includes two companion expansion struts and a joining strut to form a closed or blind loop at a proximal or distal end. This strut construction can be repeated to make the prescribed number of expansion strut pairs around the circumference in an unbroken fashion in a first expansion column of a tubular stent of present invention. A set of two consecutive closed loop expansion strut pairs in an unbroken chain in an expansion column is called expansion strut pair cycles. In this provisional application, the illustrations would contain 12 expansion strut pairs making 6 expansion strut pair cycles in a first expansion column in the cut-open 2-dimensional drawings. Each expansion strut pair cycle would have one closed loop pointing proximally and one closed loop pointing distally. Of the 12 expansion strut pairs in a first expansion column, therefor, one half of expansion strut pair closed loops point proximally and one half of expansion strut pair closed loops point distally. Although there are six (6) expansion strut pair cycles in the main illustrations of this provisional application, the number of expansion strut pair cycles can variably be changed according to a prescribed requirement of a specific stent made. This variability of having a more or less than twelve expansion strut pairs in an expansion column is within the scope of a tubular stent of present invention.

A second connecting strut column is formed of a plurality of second connecting struts. A first connecting strut in a second connecting strut column includes a connecting strut proximal section, a connecting strut distal section and a connecting strut intermediate section. A first connecting strut proximal section has two parts: a short part and a long part. A first connecting strut proximal section short part is coupled at a perpendicular or slant angle to the contralateral out side of a distal end of a first expansion strut of a first expansion strut pair in a second expansion column. A first connecting strut proximal section long part is coupled to the short part proximally at a generally perpendicular or a slant angle and to the intermediate section distally at a generally perpendicular or a slant angle. The proximal section long part generally does not parallel to the longitudinal axis of a first expansion strut of a first expansion strut pair in a second expansion column. However, the proximal section long part can be made to parallel to a longitudinal axis of a first expansion strut of a first expansion strut pair in a second expansion column. A first connecting strut distal section has two parts: a short part and a long part. A first connecting strut distal section short part is coupled at a perpendicular or slant angle to the contralateral out side of a proximal end of a second expansion strut of a first expansion strut pair in a third expansion column. A first connecting strut distal section long part is coupled to the short part distally at a generally perpendicular or a slant angle and to the intermediate section proximally at a generally perpendicular or a slant angle. A first connecting strut distal section long part generally parallel to a longitudinal axis of a second expansion strut of a first expansion strut pair in a third expansion column. However, a distal section long part can be made not to parallel to a longitudinal axis of a second expansion strut of a first expansion strut pair in a thirdexpansion column. The proximal and distal ends of a first connecting strut in a second connecting strut column point to generally opposite or different directions. A first connecting strut intermediate section proximal end is coupled at a slant angle to a first connecting strut proximal section long part and a first connecting strut intermediate section distal end is coupled at a slant angle to a first connecting strut distal section long part. The intermediate section of a first connecting strut in a second connecting strut column traverses diagonally through the inter-connecting space separating a first expansion strut pair loop in a second expansion strut column and a first expansion strut pair loop in a third expansion strut column. There is a slight angulation at the center of a first connecting strut intermediate section in a tubular stent illustrated in main figures of this provisional application. However, the intermediate section of a first connecting strut can have a straight-line or all together different configuration as long as this intermediate section serves as a diagonally coupling role between first connecting strut proximal section and first connecting strut distal section that are attached to the contralateral sides of apposed expansion strut pair loops. Furthermore, a first diagonal connector strut that connects the contralateral sides of two opposing expansion strut pair loops in respective two adjacent expansion columns can have a variety of different configurations. One such shape is an S-shape connector adapted to diagonally link the contralateral sides of two apposing expansion strut pair loops. These varied potential shape modifications of a first connecting strut in a second connecting strut column is within the scope of a tubular stent of present invention.

BRIEF DESCRIPTION OF THE DRAWINGS

FIG. 2—A larger view of FIG. 1 with more detailed marking of the stent frame structures. The expansion struts 42 in the expansion columns 32 are non-parallel to the longitudinal axis 17 of the stent 10. The expansion struts 42 in the expansion columns 32 are arranged at a sloped angle in relation to the horizontally arranged longitudinal axis 17 of the stent 10, so that the longitudinal axis of individual expansion struts 32 would not parallel to the longitudinal axis 17 of the stent 10, except for the first and the last expansion columns in which the proximal or distal segments of the expansion struts 42 have partly horizontal alignment. However, the individual expansion struts 42 in an expansion column 32 may parallel to each other, although they do not have to parallel to each other to properly function as expansion struts 42 in an expansion column 32.

DETAILED DESCRIPTION OF THE DRAWINGS

Figure 1:
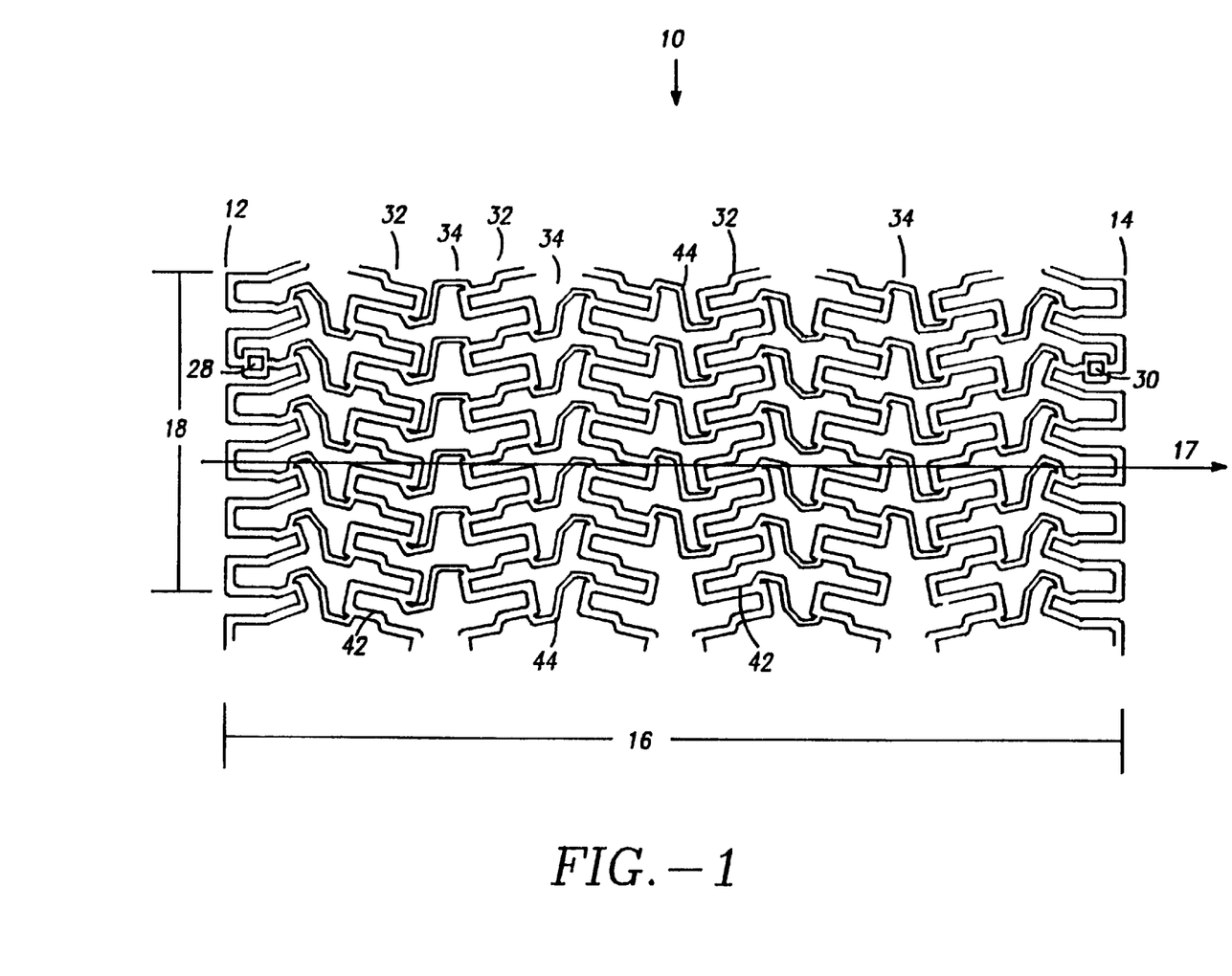
FIG. 1—A tubular stent of present invention drawn in a 2-dimensional cut-open view with the proximal end 12 on the left, the distal end 14 on the right, the circumference 18 on vertical dimension, the length and longitudinal axis 17 of the stent aligned horizontally.

FIG. 1—A tubular stent 10 of present invention is illustrated in this 2-dimensional cut open drawing with the proximal end 12 on the left side, the distal end 14 on the right side and the circumference 18 of the tubular stent 10 laid-out vertically. However, the real stent 10 is a 3-dimensional tubular object, which is illustrated in the 2-dimensional drawings to easily illustrate the key structural and design features in this FIG. 1. Computer drawn isometric and side elevation views of the tubular stent 10 will be added in the formal application.

In this illustration, the proximal end 12 of the stent 10 is on the left side and the distal end 14 is on the right with the longitudinal axis 17 and the stent length 16 of the stent 10 aligned horizontally. The circumference 18 of the stent 10 is on a vertical plane. In this figure, there are eight (8) expansion columns 32 connected by seven (7) connector columns 34, in an unbroken chain-mesh around the circumference 18 and along the stent length 16, creating a tubular structure with longitudinal axis 17 aligned horizontally. An individual expansion strut 42 in an expansion strut pair in an expansion column 32 is aligned non-horizontally in a slant slope so that the longitudinal axes 58, 59 or 60 of expansion struts 42 in an expansion strut pair in an expansion column 32 would not parallel to the longitudinal axis 17 of a tubular stent 10. Furthermore, each expansion strut 42 pair has one strut 42 with straight-line configuration, while its companion expansion strut 42 has a stair-step configuration. The dissimilar struts 42 in a same expansion strut 42 pair in an expansion column 32 in a tubular stent 10 of present invention is a unique hallmark configuration. Both the first and last expansion columns 32 have their respective marker buttons 28 and 30 in their columns 32. The first and last expansion columns 32 have modified expansion strut 42 shapes. In the first expansion column 32 on the left, the proximal half of the individual expansion struts 42 has a horizontal strut alignment to parallel with the longitudinal axis 17 of the stent 10, while the distal half of the individual expansion struts 42 has a slant angle alignment to match with the expansion strut 42 pairs in the adjacent expansion column 32 in a manner to accommodate the connector 44 attachments like rest of the stent 10. In the last expansion column on the right, the distal half of the individual expansion struts 42 has a horizontal strut alignment to parallel with the longitudinal axis of the stent 10, while the proximal half of the individual expansion struts 42 has a slant angle alignment to match with the expansion strut 42 pairs in the adjacent expansion column 32 in a manner to accommodate the connector 44 attachments like rest of the stent 10.

Figure 2:
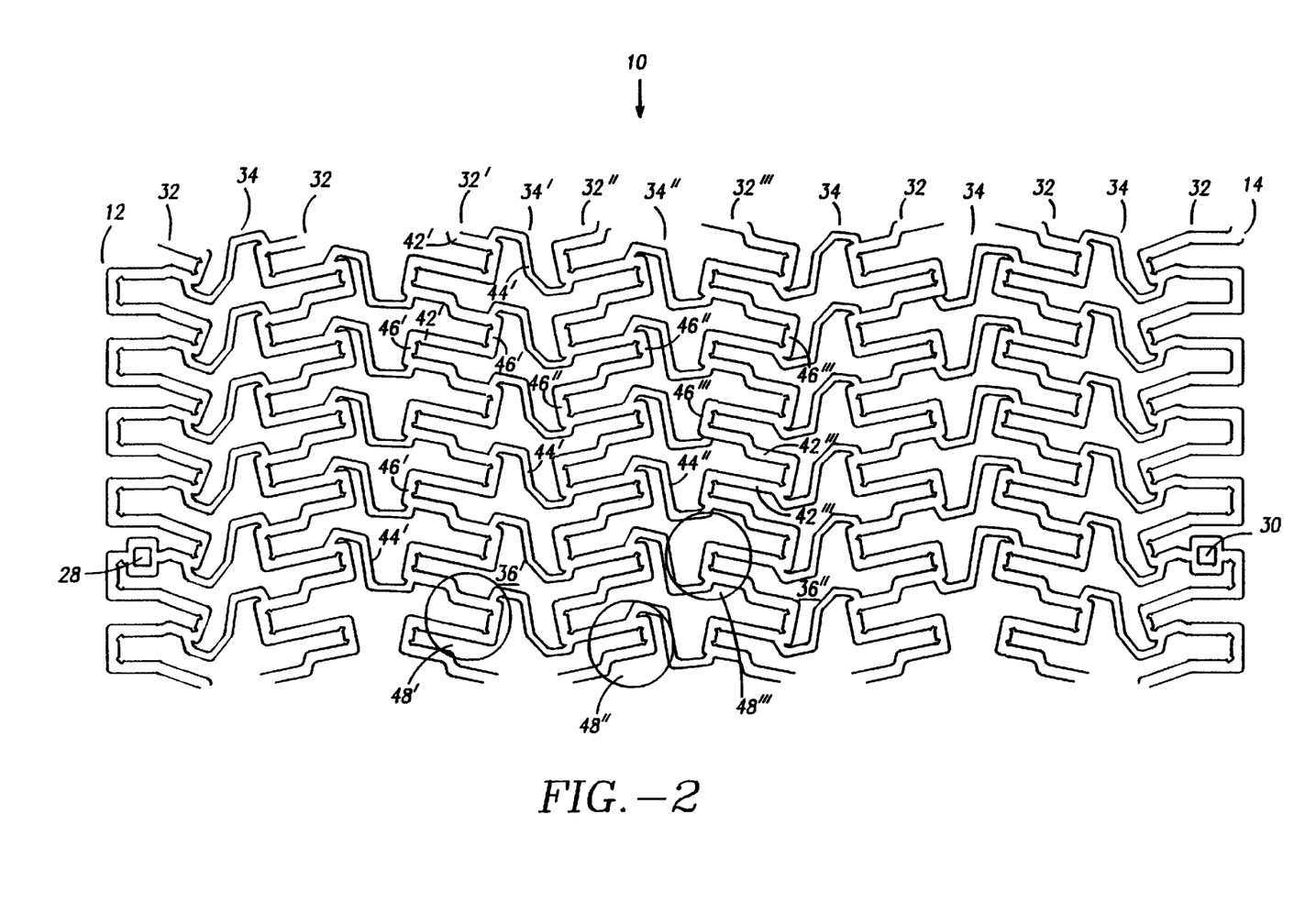

FIG. 2—This is a magnified view of FIG. 1 to add more detailed markers to the figure. An individual expansion strut 42 in an expansion strut pair in an expansion column 32 is aligned non-horizontally in a slant slope so that the longitudinal axes 58, 59 or 60 of expansion struts 42 in an expansion strut pair in an expansion column 32 would not parallel to the longitudinal axis 17 of a tubular stent 10. Furthermore, each expansion strut 42 pair has one strut 42 with straight-line configuration, while its companion expansion strut 42 has a stair-step configuration. The dissimilar struts 42 in a same expansion strut 42 pair in an expansion column 32 in a tubular stent 10 of present invention is a unique hallmark configuration. Each expansion strut 42 pair in an expansion column 32, therefor, has three different axial planes coinciding with the expansion strut 42 axes 58, 59 and 60 because of combination of one straight and one stair-step struts 42 in a same expansion strut pair.

A first expansion column 32' has twelve (12) expansion strut 42' pairs in a continuous unbroken ring around the circumference 18, made of twelve (12) expansion struts 42' and twelve joining 46' to form twelve (12) closed loop 48' at a proximal or distal end of an expansion strut 42' pair in an alternating pattern. Out of 12 expansion struts 42' in a first expansion strut column 32', there are six straight-line struts 42' and six stair-step struts 42' in an alternating pattern. A first expansion strut 42' pair in a first expansion strut column 32' consists of one straight-line expansion strut 42', one stair-step expansion strut 42' and a joining strut 46' to form a closed loop 48'. An individual expansion strut 42' in an expansion strut pair in an expansion column 32' is aligned non-horizontally in a slant slope so that the longitudinal axes 58, 59 or 60 of expansion struts 42' in an expansion strut pair in an expansion column 32' would not parallel to the longitudinal axis 17 of a tubular stent 10. Each expansion strut 42' pair in an expansion column 32', therefor, has three different axial planes coinciding with the expansion strut 42' axes 58, 59 and 60, because of having combination of one straight and one stair-step struts 42' in a single expansion strut 42' pair in an expansion column 32'.

A second expansion column 32" has twelve (12) expansion strut 42" pairs in a continuous unbroken ring around the circumference 18, made of twelve (12) expansion struts 42" and twelve joining 46" to form twelve (12) closed loop 48" at a proximal or distal end of an expansion strut 42" pair in an alternating pattern. Out of 12 expansion struts 42" in a second expansion strut column 32", there are six straight-line struts 42" and six stair-step struts 42" in an alternating pattern. A first expansion strut 42" pair in a second expansion strut column 32" consists of one straight-line expansion strut 42", one stair-step expansion strut 42" and a joining strut 46" to form a closed loop 48". An individual expansion strut 42" in an expansion strut 42" pair in an expansion column 32" is aligned non-horizontally in a slant slope so that the longitudinal axes 58, 59 or 60 of expansion struts 42" in an expansion strut 42" pair in an expansion column 32" would not parallel to the longitudinal axis 17 of a tubular stent 10. Each expansion strut 42" pair in an expansion column 32", therefor, has three different axial planes coinciding with the expansion strut 42" axes 58, 59 and 60, because of having combination of one straight and one stair-step struts 42" in a single expansion strut 42" pair in an expansion column 32".

A third expansion column 32''' has twelve (12) expansion strut 42''' pairs in a continuous unbroken ring around the circumference 18, made of twelve (12) expansion struts 42''' and twelve joining 46''' to form twelve (12) closed loop 48''' at a proximal or distal end of an expansion strut 42''' pair in an alternating pattern. Out of 12 expansion struts 42''' in a third expansion strut column 32''', there are six straight-line struts 42' and six stair-step struts 42' in an alternating pattern. A first expansion strut 42''' pair in a third expansion strut column 32''' consists of one straight-line expansion strut 42''', one stair-step expansion strut 42''' and a joining strut 46''' to form a closed loop 48'''. An individual expansion strut 42''' in an expansion strut 42''' pair in an expansion column 32''' is aligned non-horizontally in a slant slope so that the longitudinal axes 58, 59 or 60 of expansion struts 42''' in an expansion strut 42''' pair in an expansion column 32''' would not parallel to the longitudinal axis 17 of a tubular stent 10. Each expansion strut 42''' pair in an expansion column 32''', therefor, has three different axial planes coinciding with the expansion strut 42" axes 58, 59 and 60, because of having combination of one straight and one stair-step struts 42''' in a single expansion strut 42''' pair in an expansion column 32'''.

A first connecting strut column 34' has six first (6) diagonal connectors 44'. Each first diagonal connector 44' has its proximal end 62' connected to the contralateral out-side of an expansion strut pair 42' closed loop 48' pointing distally in a first expansion column 32', and its distal end 64' connected to the contralateral out-side of an expansion strut pair loop 48" pointing proximally in a second expansion column 32". The proximal end 62' of a first connecting strut 44' is attached on the opposite or contralateral side of the attachment side of the distal end 64' of a first connecting strut 44'. The proximal end 62' of a first connecting strut 44' is attached at an outside of a closed loop 48' strut pair pointing distally in a first expansion column 32', opposite (contralateral) form the attachment site of the distal end 64' of a first connecting strut 44' at an outside of a closed loop 48" pointing proximally in a second expansion column 32". The proximal end 62' points upward as it 62' attaches on the down side of a closed loop 48' in a first expansion column 32', whereas the distal end 64' points downward as it 64' attaches on the top side of a closed loop 48" in a second expansion column 32". This opposite or contralateral side or direction of the terminal ends 62' and 64' of a first connecting strut 44' are pointed or attached is a unique feature of a diagonally configured first connecting 44' in a first connecting strut column 34'.

A second connecting strut column 34" has six (6) diagonal connectors 44". Each second diagonal connector 44" has its proximal end 62" connected to the contralateral out-side of an expansion strut pair 42" closed loop 48" pointing distally in a second expansion column 32", and its distal end 64" connected to the contralateral out-side of an expansion strut pair loop 48" pointing proximally in a third expansion column 32'''. The proximal end 62" of a first connecting strut 44" is attached on the opposite or contralateral side of the attachment side of the distal end 64" of a first connecting strut 44". The proximal end 62" of a first connecting strut 44" is attached at an outside of a closed loop 48" strut pair pointing distally in a second expansion column 32", opposite (or contralateral) form the attachment site of the distal end 64" of a first connecting strut 44" at an outside of a closed loop 48''' pointing proximally in a third expansion column 32'''. The proximal end 62" points downward as it 62' attaches on the top side of a closed loop 48" in a second expansion column 32", whereas the distal end 64" points upward as it 64' attaches on the down side of a closed loop 48''' in a third expansion column 32'''. This opposite or contralateral side or direction of the terminal ends 62" and 64" of a first connecting strut 44" are pointed or attached is a unique feature of a diagonally configured first connecting 44" in a second connecting strut column 34".

When a first connector column 34' connects a first expansion column 32' to a second expansion column 32" in an unbroken chain, six (6) stent cells 36' are formed. Each stent cell 36' is consists of one (1) proximal closed loop 48' slot 38', one (1) distal closed loop 48" slot 40' and two (2) adjacent connector struts 44'. Each stent cell 36' has asymmetrical cell geometry. When a second connector column 34" connects a second expansion column 32" to a third expansion column 32''' in an unbroken chain, six (6) stent cells 36" are formed. Each stent cell 36" is consists of one (1) proximal closed loop 48" slot 38", one (1) distal closed loop 48''' slot 40" and two (2) adjacent connector struts 44". Each stent cell 36" has asymmetrical cell geometry.

Figure 3:
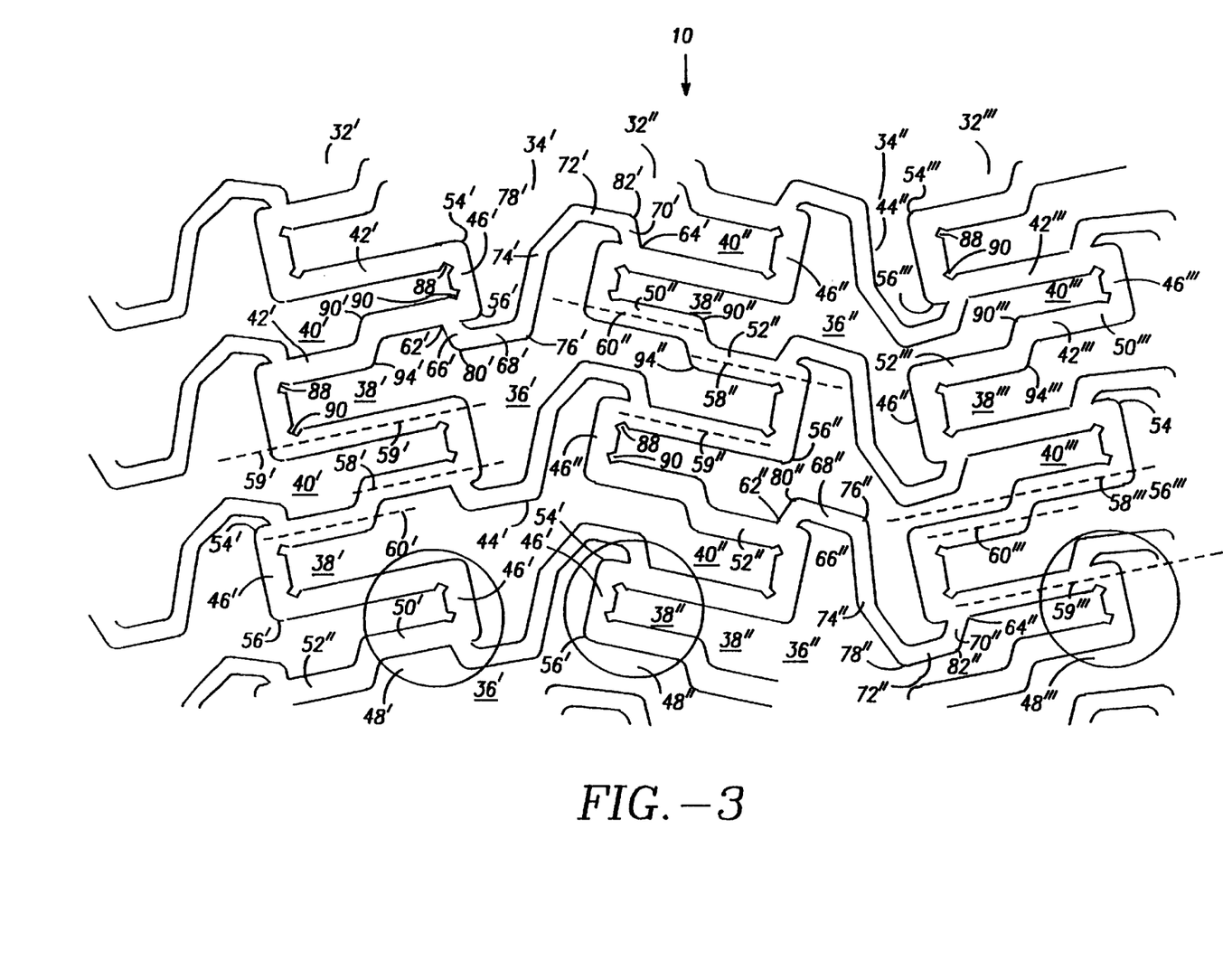
FIG. 3—A more magnified view of the basic elements of the stent 10 strut configurations with detailed markings of the key features.
Figure 4:
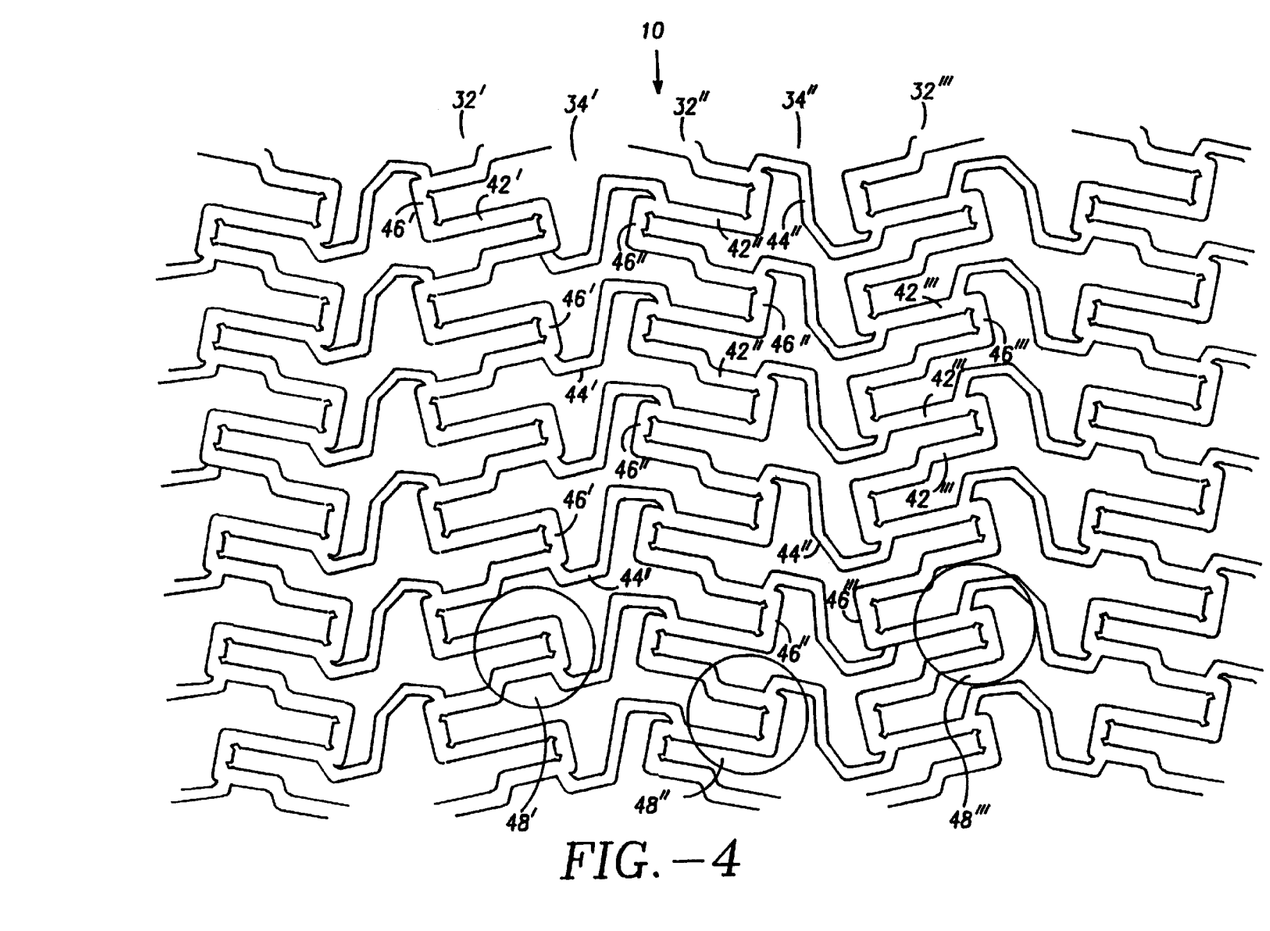
FIG. 4—Another magnified view of the tubular stent 10 of present invention in 2-dimensional cut-open drawing detailing the expansion columns and the connector columns and lengthwise stent construction along the longitudinal axis of the tubular stent 10 of present invention.

FIG. 3 & FIG. 4: This FIGS. 3 and 4 are used together to collaborate in illustrating the details of the expansion struts 42 and expansion column 32, and connecting struts 44 and connecting column 34, as well as their linking pattern to form continuous chain mesh of struts 42, 44 and stent cell 36 around the circumference 18 and along the longitudinal axis 17 of a tubular stent 10 of present invention. Both FIG. 3 and FIG. 4 are used intermingling in the following detailed description of a tubular stent 10 of present invention.

A first expansion column includes of a plurality of first expansion strut 42' pairs of a generally non-horizontal arrangement with the long axes 58', 59' and 60' of a first expansion strut 42' pairs aligned at a diagonal angle to the horizontal longitudinal axis 17 of a tubular stent 10 in the 2-dimensional drawings in this provisional application. A first expansion strut 42' pair in a first expansion column 32' has one straight-line configuration strut 42' and one stair-step configuration strut 42'; both of them being arranged non-horizontally and generally paralleling to each other, although they do not have to parallel to each other. A diagonal angle of the longitudinal axes 58', 59' and 60' of a first expansion strut 42' pairs in a first expansion column 32' point toward one direction, different from a respective diagonal angle of the longitudinal axes 58", 59" and 60" of a second expansion strut 42' pairs in a second expansion column 32". The diagonal angle of a non-horizontal expansion strut 42' pairs can be as little as 2–3 degrees or as high as 45–60 degrees from the horizontal plane and longitudinal axis 17 of a tubular stent 10. However, the preferred diagonal angle of first expansion strut 42' pair in a first expansion column is somewhere between 7–25 degrees. The longitudinal axes 58', 59' and 60' of a first and second expansion strut 42' in a first expansion strut 42' pair in a first expansion column 32' are generally parallel to each other. However, the longitudinal axes 58', 59' and 60' of a first and second expansion strut 42' in a first expansion strut 42' pair can generally be non-parallel to each other. Variations of the diagonal angle of a non-horizontal expansion strut 42' pair are within the scope of a tubular stent 10 of present invention. Both parallel alignment and non-parallel alignment of a first and a second expansion strut 42' of first expansion strut 42' pairs is within the scope of a tubular stent of present invention.

A first expansion strut 42' pair in first expansion column 42' includes a first expansion strut 42' of a straight-line configuration that is non-horizontal adjacent to a second expansion strut 42' of a stair-step configuration that is non-horizontal. A first joining strut 46' couples the first and second expansion struts 42' making a closed loop 48' at a distal end of a first expansion strut 42' pair. A second expansion strut 42' pair includes a third expansion strut 42' of a straight-line configuration that is non-horizontal adjacent to a second expansion strut 42' of a stair-step configuration that is non-horizontal. A second joining strut 46' couples a second and a third expansion strut 42' making a closed loop 48' at a proximal end of a second expansion strut 42' pair. A third expansion strut 42' pair includes a fourth expansion strut 42' of a stair-step configuration that is non-horizontal adjacent to a third expansion strut 42' of a straight-line configuration that is non-horizontal. A third joining strut 46' couples a third and a fourth expansion strut 42' making a closed loop 48' at a distal end of a third expansion strut pair. A fourth expansion strut 42' pair includes a fifth expansion strut 42' of a straight-line configuration that is non-horizontal adjacent to a fourth expansion strut 42' of a stair-step configuration that is non-horizontal. A fourth joining strut 46' couples the fourth and fifth expansion strut 42' making a closed loop 48' at a proximal end of a fourth expansion strut 42' pair. A fifth expansion strut pair includes a sixth expansion strut 42' of a stair-step configuration that is non-horizontal adjacent to a fifth expansion strut 42' of a straight-line configuration that is non-horizontal. A fifth joining strut 46' couples the fifth and sixth expansion strut 42' making a closed loop 48' at a distal end of a fifth expansion strut 42' pair. A sixth expansion strut 42' pair includes a seventh expansion strut of a straight-line configuration that is non-horizontal adjacent to a sixth expansion strut 42' of a stair-step configuration that is non-horizontal. A sixth joining strut 46' couples the sixth and seventh expansion strut 42' making a closed loop 48' at a proximal end of a sixth expansion strut pair. In the illustrations in this provisional application, there are twelve (12) first expansion strut 42' pairs arranged in an alternating and unbroken chain in a first expansion column 32'.

An expansion strut 42' pair includes two companion expansion struts 42', one having a straight-line configuration and the other having a stair-step configuration, and a joining strut 48' to form a closed or blind loop 48' at a proximal or distal end. Furthermore, these companion struts 42' are arranged non-horizontally in relation to the horizontally aligned longitudinal axis 17 of the stent 10. This expansion strut 42' pair closed loop 48' construction can be repeated to make the prescribed number of expansion strut pairs around the circumference in an unbroken fashion in a first expansion column 32' of a tubular stent 10 of present invention. A set of two consecutive closed loop 48' expansion strut 42' pairs in an unbroken chain in a first expansion column 32' is called expansion strut 42' pair cycles. In this provisional application, the figures would contain twelve (12) expansion strut 42' pairs making six (6) expansion strut 42' pair cycles in a first expansion column 32' in the cut-open 2-dimensional drawings. Each expansion strut 42' pair cycle would have one closed loop 48' pointing proximally and one closed loop 48' pointing distally. Out of twelve (12) expansion strut 42' pairs in a first expansion column 32' , therefor, one half of expansion strut 42' pair closed loops 48' point proximally and one half of expansion strut 42' pair closed loops 48' point distally. Although there are six (6) expansion strut 42' pair cycles in the figures of this provisional application, the number of expansion strut 42' pairs in a first expansion column 32' can variably be changed according to a prescribed requirement of a specific stent made. This variability of having a more or less than twelve (12) expansion strut 42' pairs in an expansion column 32 is within the scope of a tubular stent 10 of present invention.

In a first expansion column 32', each expansion strut pair consists of one straight-line strut 42', one stair-step strut 42' and a joining strut 46' to make a closed loop 48' expansion strut 42' pair. However, each expansion strut 42' pair can be made of two straight-line expansion struts 42' or of two stair-step expansion struts 42'. These mixing variation of expansion strut 42' of stair-step or straight-line configuration is within the scope of a tubular stent 10 of present invention.

A first expansion strut 42' pair first corner 54' is formed where the first joining strut 46' is coupled to the first expansion strut 42', and a first expansion strut 42' pair second corner 56' is formed where the first joining strut 46' is coupled to the second expansion strut 42'. A second expansion strut 42' pair first corner 54' is formed where the second joining strut 46' is coupled to the second expansion strut 42', and a second expansion strut 42' pair second corner 56' is formed where the second joining strut 46' is coupled to the third expansion strut 42'. A third expansion strut 42' pair first corner 54' is formed where the third joining strut 46' is coupled to the third expansion strut 42', and a third expansion strut 42' pair second corner 56' is formed where the third joining strut 46' is coupled to the fourth expansion strut 42'. A fourth expansion strut 42' pair first corner 54' is formed where the fourth joining strut 46' is coupled to the fourth expansion strut 42', and a fourth expansion strut 42' pair second corner 56' is formed where the fourth joining strut 46' is coupled to the fifth expansion strut 42'. All the expansion strut 42' pairs in a first expansion column 32' are joined with their respective joining struts 46' forming a first 54' and second 56' corner on each expansion strut 42' pair closed loop 48'.

A first expansion strut 42" pair in second expansion column 42" includes a first expansion strut 42" of a stair-step configuration that is non-horizontal adjacent to a second expansion strut 42" of a straight-line configuration that is non-horizontal. A first joining strut 46" couples the first and second expansion struts 42" making a closed loop 48" at a distal end of a first expansion strut 42" pair. A second expansion strut 42" pair includes a third expansion strut 42" of a stair-step configuration that is non-horizontal adjacent to a second expansion strut 42" of a straight-line configuration that is non-horizontal. A second joining strut 46" couples a second and a third expansion strut 42" making a closed loop 48" at a proximal end of a second expansion strut 42" pair. A third expansion strut 42" pair includes a fourth expansion strut 42" of a straight-line configuration that is non-horizontal adjacent to a third expansion strut 42" of a stair-step configuration that is non-horizontal. A third joining strut 46" couples a third and a fourth expansion strut 42" making a closed loop 48" at a distal end of a third expansion strut 42" pair. A fourth expansion strut 42" pair includes a fifth expansion strut 42" of a stair-step configuration that is non-horizontal adjacent to a fourth expansion strut 42" of a straight-line configuration that is non-horizontal. A fourth joining strut 46" couples a fourth and a fifth expansion strut 42" making a closed loop 48" at a proximal end of a fourth expansion strut 42" pair. A fifth expansion strut 42" pair includes a sixth expansion strut 42" of a straight-line configuration that is non-horizontal adjacent to a fifth expansion strut 42" of a stair-step configuration that is non-horizontal. A fifth joining strut 46" couples a fifth and a sixth expansion strut 42" making a closed loop 48" at a distal end of a fifth expansion strut 42" pair. A sixth expansion strut 42" pair includes a seventh expansion strut 42' of a stair-step configuration that is non-horizontal adjacent to a sixth expansion strut 42' of a straight-line configuration that is non-horizontal. A sixth joining strut 46" couples a sixth and a seventh expansion struts 42" making a closed loop 48" at a proximal end of a sixth expansion strut 42" pair. In the figures in this provisional application, there are twelve (12) first expansion strut 42" pairs arranged in an alternating and unbroken chain in a second expansion column 32".

An expansion strut 42" pair in a second expansion column 32" includes two companion expansion struts 42", one having a straight-line configuration and the other having a stair-step configuration, and a joining strut 46" to form a closed or blind loop 48" at a proximal or distal end of a first expansion strut 42' pair. Furthermore, these companion struts 42" are arranged non-horizontally in relation to the horizontally aligned longitudinal axis 17 of the stent 10. This construction process of making a closed loop 48" expansion strut 42" pair in an alternating proximal or distal direction can be repeated to make the prescribed number of closed loop 48" expansion strut 42" pairs around the circumference 18 in an unbroken fashion in a second expansion column 32" of a tubular stent 10 of present invention. A set of two consecutive closed loop 48" expansion strut 42" pairs in an unbroken chain in a second expansion column 32" is called expansion strut 42" pair cycles. In this provisional application, the figures would contain twelve (12) expansion strut 42" pairs in a second expansion column 32" making six (6) expansion strut 42" pair cycles in a second expansion column 32" in the cut-open 2-dimensional drawings. Each expansion strut 42" pair cycle in a second expansion column 32" would have one closed loop 48" pointing proximally and one closed loop 48" pointing distally. Out of twelve (12) expansion strut 42' pairs in a second expansion column 32", therefor, one half of expansion strut 42" pair closed loops 48" point proximally and one half of expansion strut 42" pair closed loops 48" point distally in an alternating pattern. Although there are six (6) expansion strut 42" pair cycles in a second expansion column 32" in the figures of this provisional application, the number of expansion strut 42" pairs in a second expansion column 32" can variably be changed according to a prescribed requirement of a specific stent made. This variability of having a more or less than twelve (12) expansion strut 42" pairs in a second expansion column 32" is within the scope of a tubular stent 10 of present invention.

In a second expansion column 32", each expansion strut 42" pair consists of one straight-line strut 42", one stair-step strut 42" and a joining strut 46" to make a closed loop 48". However, each expansion strut 42" pair can be made of two straight-line expansion struts 42" or of two stair-step expansion struts 42". These mixing variation of expansion strut 42" of stair-step or straight-line configuration is within the scope of a tubular stent 10 of present invention.

A first expansion strut 42" pair first corner 54" in a second expansion column 32" is formed where the first joining strut 46" is coupled to the first expansion strut 42" , and a first expansion strut 42" pair second corner 56" is formed where the first joining strut 46" is coupled to the second expansion strut 42". A second expansion strut 42" pair first corner 54" is formed where the second joining strut 46" is coupled to the second expansion strut 42", and a second expansion strut 42" pair second corner 56" is formed where the second joining strut 46" is coupled to the third expansion strut 42". A third expansion strut 42" pair first corner 54" is formed where the third joining strut 46" is coupled to the third expansion strut 42', and a third expansion strut 42" pair second corner 56" is formed where the third joining strut 46" is coupled to the fourth expansion strut 42". A fourth expansion strut 42" pair first corner 54" is formed where the fourth joining strut 46" is coupled to the fourth expansion strut 42", and a fourth expansion strut 42" pair second corner 56" is formed where the fourth joining strut 46" is coupled to the fifth expansion strut 42". All the expansion strut 42" pairs in a second expansion column 32" are joined with their respective joining struts 46" forming a first 54" and second 56" corner on each expansion strut 42" pair closed loop 48".

A first connecting strut column 34' is formed of a plurality of first connecting struts 44'. A first connecting strut 44' in a first connecting strut column 43' includes a connecting strut proximal section 66' and 68', a connecting strut distal section 70' and 72' and a connecting strut intermediate section 74'. A first connecting strut proximal section has two parts: a short part 66' and a long part 68'. A first connecting strut proximal end 62' of a proximal section short part 66' is coupled at a perpendicular or slant angle to the contralateral out side of a distal end of a second expansion strut 42' of a first expansion strut 42' pair in a first expansion column 32'. A first connecting strut proximal section long part 68' is coupled to the short part 66' proximally at a generally perpendicular or a slant angle in a junction 80' and to the intermediate section 74' distally at a generally perpendicular or a slant angle in a junction 76'. The proximal section long part 68' generally do not parallel to the longitudinal axis 58' of a second expansion strut 42' of a first expansion strut 42' pair in a first expansion column 32'. However, the proximal section long part 68' can be made to parallel to a longitudinal axis 58' of a second expansion strut 42' of a first expansion strut 42' pair in a first expansion column 32'. A first connecting strut distal section has two parts: a short part 70' and a long part 72'. A first connecting strut distal end 64' of a distal section short part 70' is coupled at a perpendicular or slant angle to the contralateral out side of a proximal end of a second expansion strut 42" of a first expansion strut 42" pair in a second expansion column 32". A first connecting strut distal section long part 72' is coupled to the short part 70' distally at a generally perpendicular or a slant angle in a junction 82' and to the intermediate section 74' proximally at a generally perpendicular or a slant angle in a junction 78'. A distal section long part 72' generally parallels to a longitudinal axis 59" of a second expansion strut 42" of a first expansion strut 42" pair in a second expansion column 32". However, a first connecting strut 44' distal section long part 72' can be made not to parallel to a longitudinal axis 59' of a second expansion strut 42" of a first expansion strut 42' pair in a second expansion column 32". The proximal 62' and distal 64' end of a first connecting strut 44' point generally to opposite or different directions. This is the reason for contralateral attachment sites of the proximal 62' and distal 64' terminal ends of a first connecting strut 44'. A first connecting strut 44' intermediate section 74' proximal end is coupled at a slant angle to a first connecting strut proximal section long part 68' in a junction 76' and a first connecting strut intermediate section 74' distal end is coupled at a slant angle to a first connecting strut 44' distal section long part 72' in a junction 78'. The intermediate section 74' of a first connecting strut 44' traverses diagonally through the inter-connecting space separating a first expansion strut 42' pair closed loop 48' in a first expansion column 32' and a first expansion strut 42' pair closed loop 48" in a second expansion column 32". There is a slight angulation at the center of the intermediate section 74' of a first connecting strut 44' in a tubular stent 10 illustrated in the figures of this provisional application. However, the intermediate section 74' of a first connecting strut 44' can have a straight-line or an all together different configuration as long as this intermediate section 74' serves as a diagonally coupling role between first connecting strut 44' proximal section 68' and first connecting strut 44' distal section 72', that are attached to contralateral sides on the apposed expansion strut pair loops through the angled terminal ends 62' and 64' of opposing directions. Furthermore, a first connector strut 44' in a first connecting strut column 34' that connects the contralateral sides of two apposing expansion strut pair loops 48' and 48" in respective two adjacent expansion columns 32' and 32" can have a variety of different configurations. One such shape is an S-shape first connecting strut 44' adapted to diagonally link the contralateral sides on two apposing expansion strut pair loops 48' and 48". These varied potential shape modifications of a first connecting strut 44' in a first connecting strut column 34' for a contralateral attachments through a diagonal intermediate section is within the scope of a tubular stent 10 of present invention.

A second, third, through sixth connecting strut 44' in a first connecting strut column 34' has identical connecting strut configuration like a first connecting strut 44' in a first connecting strut column 34' as described in the foregoing paragraphs. A second, third through sixth connecting strut 44' in a first connecting strut column 34' connects a first expansion column 32' to a second expansion column 32" at their respective apposing contralateral coupling locations to make a full and unbroken ring of a first connecting column 34' around the circumference 18 of a tubular stent 10 of the present invention. A second connecting strut 44', in a similar manner as a first connecting strut 44' described above, connects a third expansion strut 42' pair closed loop 48' in a first expansion column 32' to a fourth expansion strut 42" pair closed loop 48" in a second expansion column 32". A third connecting strut 44' connects a fifth expansion strut 42' pair closed loop 48' in a first expansion column 32' to a sixth expansion strut 42" pair closed loop 48" in a second expansion column 32". A fourth connecting strut 42' connects a seventh expansion strut 42' pair closed loop 48' in a first expansion column 32' to an eighth expansion strut 42" pair closed loop 48" in a second expansion column 32". Likewise, a fifth connecting strut 44' and a sixth connecting strut 44' connects the ninth expansion strut 42' pair closed loops 48' to tenth expansion strut 42" pair closed loops 48" and eleventh expansion strut 42' pair closed loops 48' to twelfth expansion strut 42" pair closed loops 48", respectively. A first connecting strut 44' column 34' connects a first expansion column 32' to a second expansion column 32" to form an unbroken chain mesh consist of expansion 42', 42" struts and connecting struts 44'. The connecting strut column 34' connects a first expansion column 32' to a second expansion column 32" creating six (6) closed stent cells 36' in a first connecting column 34' around the circumference 18 of a short tubular structure with a longitudinal axis 17 formed by two expansion columns 32' and 32" and one connecting strut column 34'. The closed cells 36' in a first connecting strut column 34' has similar cell geometry with a proximal slot 38' inside an expansion strut 42' pair closed loop 48' and a distal slot 40' inside an expansion strut 42" pair closed loop 48". Each of the stent cells 36' in a first connector strut column 34' has an asymmetrical cell geometry. However, in certain circumstances, the stent cell 36' geometry may have rotational symmetry.

Other form or shape of a connector, beside the diagonal connector 44' described in this application, configured to attach to the contralateral sides on apposing expansion strut 42' pair closed loops 48' can be used to couple a first 32' and second 32" expansion columns of non-parallel arrangement. The variation of any connector configuration contralaterally connecting two apposing expansion strut 42 pair closed loops 48 in two adjacent expansion columns 32 of non-parallel arrangement is within the scope of a tubular stent 10 of present invention.

A first expansion strut 42''' pair in a third expansion column 32''' includes a first expansion strut 42''' of a stair-step configuration that is non-horizontal adjacent to a second expansion strut 42''' of a straight-line configuration that is non-horizontal. A first joining strut 46''' couples the first and second expansion struts 42''' making a closed loop 48''' at a proximal end of the first expansion strut 42''' pair. A second expansion strut 42''' pair includes a third expansion strut 42''' of a stair-step configuration that is non-horizontal adjacent to a second expansion strut 42''' of a straight-line configuration that is non-horizontal. A second joining strut 46''' couples the second and third expansion struts 42''' making a closed loop 48''' at a distal end of a second expansion strut 42''' pair. A third expansion strut 42''' pair includes a fourth expansion strut 42" of a straight-line configuration that is non-horizontal adjacent to a third expansion strut 42" of a stair-step configuration that is non-horizontal. A third joining strut 46''' couples the third and fourth expansion struts 42''' making a closed loop 48''' at a proximal end of a third expansion strut 42''' pair. A fourth expansion strut 42''' pair includes a fifth expansion strut 42''' of a stair-step configuration that is non-horizontal adjacent to a fourth expansion strut 42''' of a straight-line configuration that is non-horizontal. A fourth joining strut 46''' couples the fourth and fifth expansion struts 42''' making a closed loop 48''' at a distal end of a fourth expansion strut 42''' pair. A fifth expansion strut 42''' pair includes a sixth expansion strut 42''' of a straight-line configuration that is non-horizontal adjacent to a fifth expansion strut 42''' of a stair-step configuration that is non-horizontal. A fifth joining strut 46''' couples the fifth and sixth expansion struts 42''' making a closed loop 48''' at a proximal end of a fifth expansion strut 42''' pair. A sixth expansion strut 42''' pair includes a seventh expansion strut 42''' of a stair-step configuration that is non-horizontal adjacent to a sixth expansion strut 42''' of a straight-line configuration that is non-horizontal. A sixth joining strut 46''' couples the sixth and seventh expansion struts 42''' making a closed loop 48''' at a distal end of a sixth expansion strut pair. In the illustrations in this provisional application, there are 12 third expansion strut 42''' pairs arranged in an unbroken chain in a third expansion column 32'''.

An expansion strut 42''' pair includes two companion expansion struts 42''' and a joining strut 46''' to form a closed or blind loop 48''' at a proximal or distal end of a third expansion strut 42''' pair. This strut 42''' pair and closed loop 48''' construction can be repeated in an alternating and unbroken pattern to make the prescribed number of expansion strut 42''' pairs around the circumference 18 in a third expansion column 32''' of a tubular stent 10 of present invention. A set of two consecutive closed loop 48''' expansion strut 42''' pairs in an unbroken chain in an expansion column is called expansion strut pair cycles. In this provisional application, the illustrations would contain 12 expansion strut 42''' pairs making 6 expansion strut pair 42''' cycles in a third expansion column 32''' in the cut-open 2-dimensional drawings. Each expansion strut 42''' pair cycle would have one closed loop 48''' pointing proximally and one closed loop 48''' pointing distally. Of the 12 expansion strut 42''' pairs in a third expansion column 32''', therefor, one half of expansion strut 42''' pair closed loops 48''' point proximally and one half of expansion strut 42''' pair closed loops 48''' point distally. Although there are six (6) expansion strut 42''' pair cycles in the main illustrations of this provisional application, the number of expansion strut 42''' pair cycles can variably be changed according to a prescribed requirement of a specific stent 10 made. This variability of having a more or less than twelve unbroken expansion strut 42''' pairs in an expansion column 32''' is within the scope of a tubular stent 10 of present invention.

In a third expansion column, each expansion strut pair consists of one straight-line strut 42''', one stair-step strut 42''' and a joining strut 46''' to make a closed loop 48''' strut 42''' pair. However, each expansion strut 42''' pair can be made of two straight-line expansion struts 42'' or of two stair-step expansion struts 42'''. These mixing variation of expansion strut 42''' pair configuration of stair-step or straight-line is within the scope of a tubular stent 10 of present invention.

A first expansion strut 42''' pair first corner 54''' is formed where the first joining strut 46''' is coupled to the first expansion strut 42''', and a first expansion strut 42''' pair second corner 56''' is formed where the first joining strut 46''' is coupled to the second expansion strut 42'''. A second expansion strut 42''' pair first corner 54''' is formed where the second joining strut 46''' is coupled to the second expansion strut 42''', and a second expansion strut 42''' pair second corner 56''' is formed where the second joining strut 46''' is coupled to the third expansion strut 42'''. A third expansion strut 42''' pair first corner 54''' is formed where the third joining strut 46''' is coupled to the third expansion strut 42''', and a third expansion strut 42''' pair second corner 56''' is formed where the third joining strut 42''' is coupled to the fourth expansion strut 42'''. A fourth expansion strut 42''' pair first corner 54''' is formed where the fourth joining strut 46''' is coupled to the fourth expansion strut 42''', and a fourth expansion strut 42''' pair second corner 56''' is formed where the fourth joining strut 42''' is coupled to the fifth expansion strut 42'''. All the expansion strut 42''' pairs in a third expansion column 32''' are joined with their respective joining struts 46''' forming a first 54''' and second 56''' corner in each expansion strut 42''' pair closed loop 48''' in a third expansion column 32'''.

A second connecting strut column 34'' is formed of a plurality of second connecting strut 44''. A first connecting strut 44'' in a second connecting strut column 34'' includes a connecting strut 44'' proximal section 66'', 68'', a connecting strut distal section 70'', 72'' and a connecting strut 44'' intermediate section 74''. A first connecting strut 44'' proximal section has two parts: a short part 66'' and a long part 68''. A first connecting strut 44'' proximal end 62'' of short part 66'' is coupled at a perpendicular or slant angle to the contralateral out side of a distal end of a first expansion strut 42'' of a first expansion strut 42'' pair closed loop 48'' in a second expansion column 32''. A first connecting strut 44'' proximal section long part 68'' is coupled to the short part 66'' proximally at a generally perpendicular or a slant angle and to the intermediate section 74'' distally at a generally perpendicular or a slant angle. The proximal section long part 68'' generally does not parallel to the longitudinal axis 58'' of a first expansion strut 42'' of a first expansion strut 42'' pair in a second expansion column 32''. However, the proximal section long part 68'' can be made to parallel to a longitudinal axis 58'' of a first expansion strut 42'' of a first expansion strut 42'' pair in a second expansion column 32''. A first connecting strut 44'' distal section has two parts: a short part 70'' and a long part 72''. A first connecting strut 44'' distal section short part 70'' is coupled at a perpendicular or slant angle to the contralateral out side of a proximal end of a second expansion strut 42''' of a first expansion strut 42''' pair in a third expansion column 32'''. A first connecting strut 44'' distal section long part 72'' is coupled to the short part 70'' distally at a generally perpendicular or a slant angle and to the intermediate section 74'' proximally at a generally perpendicular or a slant angle. A first connecting strut 44'' distal section long part 72'' generally parallels to a longitudinal axis 59''' of a second expansion strut 42''' of a first expansion strut 42''' pair in a third expansion column 32'''. However, a distal section long part 72'' can be made not to parallel to a longitudinal axis 59''' of a second expansion strut 42''' of a first expansion strut 42''' pair in a third expansion column 32'''. The proximal 62'' and distal 64'' ends of a first connecting strut 44'' in a second connecting strut column 34'' point to generally opposite or different directions. A first connecting strut 44'' intermediate section 74'' proximal end is coupled at a slant angle to a first connecting strut 44'' proximal section long part 68'' and a first connecting strut 44'' intermediate section 74'' distal end is coupled at a slant angle to a first connecting strut 44'' distal section long part 72''. The intermediate section 74'' of a first connecting strut 44'' in a second connecting strut column 34'' traverses diagonally through the inter-connecting space separating a first expansion strut 42'' pair closed loop 48'' in a second expansion strut column 32" and a first expansion strut 42'" pair closed loop 48'" in a third expansion strut column 32'". There is a slight angulation at the center of a first connecting strut intermediate section 74" in the figures of this provisional application. However, the intermediate section 74" of a first connecting strut 44" can have a straight-line or all together different configuration as long as this intermediate section 74" serves as a diagonally coupling role between first connecting strut proximal section 68" and first connecting strut distal section 72" that are attached to the contralateral sides of the apposed expansion strut pair loops 46", 46'". Furthermore, a first diagonal connector strut 44" that connects the contralateral sides of two opposing expansion strut pair loops 48", 48'" in respective two adjacent expansion columns 32", 32'" can have a variety of different configurations. One such shape is an S-shape connector adapted to diagonally link the contralateral sides of two apposing expansion strut pair loops 48", 48'". These varied potential shape modifications of a first connecting strut 44" in a second connecting strut column 34" is within the scope of a tubular stent 10 of present invention.

A second, third, through sixth connecting strut 44" in a second connecting strut column 34" has identical connecting strut 44" configuration like a first connecting strut 44" in a second connecting strut column 34" as described in the foregoing paragraph. A second, third through sixth connecting strut 44" in a second connecting column 34" connects a second expansion column 32" to a third expansion column 32'" at their respective contralateral coupling locations of respective apposing expansion strut pair loops 48", 48'" to make a full and unbroken ring of connecting column 34" around the circumference 18 of a tubular stent 10 of the present invention. A second connecting strut 44", in a similar manner as a first connecting strut 44" described above, connects a third expansion strut pair loop 48" in a second expansion column 32" to a third expansion strut pair loop 48'" in a third expansion column 32'". A third connecting strut 44" connects a fifth expansion strut pair loop 48" in a second expansion column 32" to a fifth expansion strut pair loop 48'" in a third expansion column 32'". A fourth connecting strut 44" connects a seventh expansion strut pair loop 48" in a second expansion column 32" to a seventh expansion strut pair loop 48'" in a third expansion column 32'". Likewise, a fifth connecting strut 44" and a sixth connecting strut 44" connects the ninth expansion strut pair loops 48", 48'", the eleventh expansion strut pair loops 48", 48'", respectively of second 32" and third 32'" expansion columns. /// A second connecting strut 44" column 34" connects a second expansion column 32" to a third expansion column 32'" to form an unbroken chain mesh consist of expansion 42", 42'" struts and connecting struts 44". The connecting strut column 34" connects a second expansion column 32" to a third expansion column 32" creating six (6) closed stent cells 36" in a second connecting column 34" around the circumference 18 of a short tubular structure with a longitudinal axis 17 formed by two expansion columns 32" and 32'" and one connecting strut column 34". The closed cells 36" in a second connecting strut column 34" has similar cell geometry with a proximal slot 38" inside an expansion strut 42" pair closed loop 48" and a distal slot 40" inside an expansion strut 42'" pair closed loop 48'". Each of the stent cells 36" in a second connecting strut column 34" has asymmetrical cell geometry. However, in certain circumstances, the stent cell 36" geometry may have rotational symmetry.

Other form or shape of a connector 44", beside the diagonal connector 44" described in this application, configured to attach to the contralateral sides of apposing expansion strut pair loops 48", 48'" can be used to couple a second 32" and a third 32" expansion column of non-parallel arrangement. The variation of any connector configuration contralaterally connecting two apposing expansion strut pair loops in two adjacent expansion columns is within the scope of a tubular stent 10 of present invention.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

I claim:

1. An intra-luminal vascular stent in a non-expanded state with a longitudinal axis, comprising:

a plurality of expansion strut pairs forming a first expansion column, each of an expansion strut pair including a stair-step expansion strut, a straight-line expansion strut and a joining strut coupling an end of the strut pair forming a cell slot, each of the expansion strut pair having three longitudinal axes that are aligned in a non-parallel relationship to the stent longitudinal axis;

a plurality of expansion strut pairs forming a second expansion column, each of an expansion strut pair including a straight-line expansion strut, a stair-step expansion strut and a joining strut coupling an end of the strut pair forming a cell slot, each of the expansion strut pair having three longitudinal axes that are aligned in a non-parallel relationship to the stent longitudinal axis; and a plurality of serial connecting struts forming a first serial connecting strut column and including a first serial connecting strut, the first serial connecting strut column coupling the first expansion column to the second expansion column.

2. The stent of claim 1, wherein the first serial connecting strut includes a proximal portion including a proximal stem and a linear section, a distal portion including a distal stem and a linear section, and an intermediate section that couples the proximal and distal portions.

3. The stent of claim 2, wherein the intermediate section of the first serial connecting strut includes a proximal linear section and a distal linear section.

4. The stent of claim 3, wherein in the first serial connecting strut the linear section of the proximal portion has a longitudinal axis that is parallel to the longitudinal axis of the stent.

5. The stent of claim 4, wherein in the first serial connecting strut, the linear section of the distal portion has a longitudinal axis that is parallel to a longitudinal axis of the straight-line expansion strut of the second expansion column.

6. The stent of claim 3, wherein the proximal stem of the first connecting strut is contralaterally coupled to a side of distal portion of the stair-step expansion strut of the first expansion column, and the distal stem of the first serial connecting strut is contralaterally coupled to a side of a proximal portion of the straight-line expansion strut of the second expansion column.

7. The stent of claim 6, wherein the proximal stem of the first connecting strut is contralaterally coupled to a second side of a distal portion of the stair-step expansion strut of the first expansion column, and the distal stem of the first serial connecting strut is contralaterally coupled to a first side of a proximal portion of the straight-line expansion strut of the second expansion column.

8. The stent of claim 6, wherein the proximal stem of the first connecting strut is contralaterally coupled to a second side of a distal portion of the stair-step expansion strut of the first expansion column, and the distal stem of the first serial connecting strut is contralaterally coupled to a first side of a proximal portion of the stair-step expansion strut of the second expansion column.

9. The stent of claim 6, wherein the proximal stem of the first connecting strut is contralaterally coupled to a second side of a distal portion of the straight-line expansion strut of the first expansion column, and the distal stem of the first serial connecting strut is contralaterally coupled to a proximal portion of a first side of the straight-line expansion strut of the second expansion column.

10. The stent of claim 3, wherein the intermediate portion of the first serial connecting strut diagonally couples the proximal and distal portions of the first serial connecting strut.

11. The stent of claim 3, wherein the intermediate portion of the first serial connecting strut diagonally couples a distal portion of the stair-step expansion strut of the first expansion column to a proximal portion of the straight-line expansion strut of the second expansion column.

12. The stent of claim 3, wherein the intermediate portion of the first serial connecting strut diagonally couples a distal portion of the stair-step expansion strut of the first expansion column to a proximal portion of the stair-step strut of the second expansion column.

13. The stent of claim 3, wherein the first serial connecting strut contralaterally couples to a side of a distal portion of the stair-step expansion strut of the first expansion column to a side of a proximal portion of the straight-line expansion strut of the second expansion column.

14. The stent of claim 3, wherein the first serial connecting strut contralaterally couples to a side of a distal portion of the stair-step expansion strut of the first expansion column to a side of a proximal portion of the stair-step expansion strut of the second expansion column.

15. The stent of claim 3, wherein the first serial connecting strut contralaterally couples to a side of a distal portion of the straight-line expansion strut of the first expansion column to a side of a proximal portion of the straight-line expansion strut of the second expansion column.

16. The stent of claim 3, wherein the proximal stem of the first connecting strut is contralaterally coupled to a side of distal portion of the stair-step expansion strut of the first expansion column, and the distal stem of the first serial connecting strut is contralaterally coupled to a side of a proximal portion of the stair-step expansion strut of the second expansion column.

17. The stent of claim 3, wherein the proximal stem of the first connecting strut is contralaterally coupled to a side of distal portion of the straight-line expansion strut of the first expansion column, and the distal stem of the first serial connecting strut is contralaterally coupled to a side of a proximal portion the straight-line expansion strut of the second expansion column.

18. The stent of claim 1, wherein the first expansion column and the second expansion column are coupled by the first serial connecting strut column to form a plurality of asymmetric cells.

19. The stent of claim 18, wherein each of an asymmetric cell includes a proximal cell slot formed in the first expansion column and a distal cell slot formed in the second expansion column.

20. The stent of claim 19, wherein the proximal cell slot has a longitudinal axis that is non-parallel to a longitudinal axis of the distal cell slot.

21. The stent of claim 20, wherein in the second expansion column a longitudinal axis of the stair-step expansion strut has a first and a second longitudinal axis each being parallel to a longitudinal axis of the straight-line expansion strut.

22. The stent of claim 19, wherein the axis of the proximal slot and the axis of the distal slot are non-parallel to each other and are not parallel to the longitudinal axis of the stent.

23. The stent of claim 1, wherein in the first expansion column a longitudinal axes of the stair-step expansion strut has a first and a second longitudinal axis each being parallel to a longitudinal axis of the straight-line expansion strut.

24. The stent of claim 23, wherein the longitudinal axes of the expansion struts in the first expansion column are non-parallel to the longitudinal axes of the expansion struts in the second expansion column.

25. The stent of claim 1, wherein the cell slots in the first and second expansion columns are asymmetric cell slots.

26. The stent of claim 1, wherein in the first expansion column a longitudinal axes of the stair-step expansion strut has a first and a second longitudinal axis each being non-parallel to a longitudinal axis of the straight-line expansion strut.

27. An intra-luminal vascular stent in a non-expanded state with a longitudinal axis, comprising:

a plurality of expansion strut pairs forming a first expansion column, each of an expansion strut pair including a stair-step expansion strut, a straight-line expansion strut and joining strut coupling an end of the strut pair forming a cell slot, each of the expansion strut pair having three longitudinal axes that are aligned in a non-parallel relationship to the stent longitudinal axis;

a plurality of expansion strut pairs forming a second expansion column, each of an expansion strut pair including a straight-line expansion strut, a stair-step expansion strut and a joining strut coupling an end of the strut pair forming a cell slot, each of the expansion strut pair having three longitudinal axes that are aligned in a non-parallel relationship to the stent longitudinal axis;

a first serial connecting strut column formed of a plurality of serial connecting struts and including a first serial connecting strut, the first serial connecting strut column coupling the first expansion column to the second expansion column;

a plurality of expansion strut pairs forming a third expansion column, each of an expansion strut pair including a stair-step expansion strut, a straight-line expansion strut and joining strut coupling an end of the strut pair forming a cell slot, each of the expansion strut pair having three longitudinal axes that are aligned in a non-parallel relationship to the stent longitudinal axis; and a plurality of serial connecting struts forming a second serial connecting strut column and including a second serial connecting strut, the second serial connecting strut column coupling the second expansion column to the third expansion column.

28. The stent of claim 27, wherein the first and second expansion columns and the first serial connecting strut column form a first set of asymmetric cells.

29. The stent of claim 28, wherein the second and third expansion columns and the second serial connecting strut column form a second set of asymmetric cells.

30. The stent of claim 29, wherein each of an asymmetric cell in the first set includes a proximal slot formed between a pair of adjacent expansion struts in the first expansion column and a distal slot formed between a pair of adjacent expansion struts in the second expansion column, and each of an asymmetric cell in the second set includes a proximal slot formed between a pair of adjacent expansion struts in the second expansion column and a distal slot formed between a pair of adjacent expansion struts in the third expansion column.

31. The stent of claim 30, wherein in an asymmetric cell each proximal cell slot has a longitudinal axis that is non-parallel to a longitudinal axis of the distal cell slot.

32. The stent of claim 31, wherein in the third expansion column a longitudinal axis of the stair-step expansion strut has a first and a second longitudinal axis each being parallel to a longitudinal axis of the straight-line expansion strut.

33. The stent of claim 32, wherein the longitudinal axes of the expansion struts in the second expansion column are non-parallel to the longitudinal axes of the expansion struts in the third expansion column.

34. The stent of claim 27, wherein in the second expansion column a longitudinal axes of the stair-step expansion strut has a first and a second longitudinal axis each being non-parallel to a longitudinal axis of the straight-line expansion strut.

35. The stent of claim 34, wherein the second serial connecting strut includes a proximal portion including a proximal stem and a linear section, a distal portion including a distal stem and a linear section, and an intermediate section that couples the proximal and distal portions.

36. The stent of claim 35, wherein in the second serial connecting strut, the linear section of the proximal portion has a longitudinal axis that is parallel to the longitudinal axis of the stent.

37. The stent of claim 36, wherein in the second serial connecting strut, the linear section of the distal portion has a longitudinal axis that is parallel to a longitudinal axis of the straight-line expansion strut of the second expansion column.

38. The stent of claim 35, wherein the intermediate section of the second serial connecting strut includes a proximal linear section and a distal linear section.

39. The stent of claim 35, wherein in the second serial connecting strut column, the intermediate portion of the second serial connecting strut diagonally couples the proximal and distal portions of the first serial connecting strut.

40. The stent of claim 35, wherein the intermediate portion of the second serial connecting strut diagonally couples a side of a distal portion of the stair-step expansion strut of the second expansion column to a side of a proximal portion of the straight-line expansion strut of the third expansion column.

41. The stent of claim 35, wherein the intermediate portion of the second serial connecting strut diagonally couples a side of a distal portion of the stair-step expansion strut of the second expansion column to a side of a proximal portion of the stair-step strut of the third expansion column.

42. The stent of claim 35, wherein the second serial connecting strut contralaterally couples a side of a distal portion of the stair-step expansion strut of the second expansion column to a side of a proximal portion of the straight-line expansion strut of the third expansion column.

43. The stent of claim 35, wherein the second serial connecting strut contralaterally couples a side of a distal portion of the stair-step expansion strut of the second expansion column to a side of a proximal portion of the stair-step expansion strut of the third expansion column.

44. The stent of claim 35, wherein the second serial connecting strut contralaterally couples a side of a distal portion of the straight-line expansion strut of the second expansion column to a side of a proximal portion of the straight-line expansion strut of the third expansion column.

45. The stent of claim 35, wherein the proximal stem of the second serial connecting strut is contralaterally coupled to a side of distal portion of the stair-step expansion strut of the second expansion column, and the distal stem of the second serial connecting strut is contralaterally coupled to side of a proximal portion of the straight-line expansion strut of the third expansion column.

46. The stent of claim 35, wherein the proximal stem of the second serial connecting strut is contralaterally coupled to a side of a distal portion of the stair-step expansion strut of the second expansion column, and the distal stem of the second serial connecting strut is contralaterally coupled to a side of a proximal portion of the stair-step expansion strut of the third expansion column.

47. The stent of claim 35, wherein the proximal stem of the second serial connecting strut is contralaterally coupled to a side of a distal portion of the straight-line expansion strut of the second expansion column, and the distal stem of the second serial connecting strut is contralaterally coupled to a side of proximal portion the straight-line expansion strut of the third expansion column.

48. The stent of claim 35, wherein the proximal stem of the second serial connecting strut is contralaterally coupled to a second side of a distal portion of the stair-step expansion strut of the first expansion column, and the distal stem of the second serial connecting strut is contralaterally coupled to a first side of a proximal portion of the straight-line expansion strut of the third expansion column.

49. The stent of claim 35, wherein the proximal stem of the second connecting strut is contralaterally coupled to a second side of a distal portion of the stair-step expansion strut of the second expansion column, and the distal stem of the second serial connecting strut is contralaterally coupled to a first side of a proximal portion of the stair-step expansion strut of the third expansion column.

50. The stent of claim 35, wherein the proximal stem of the second connecting strut is contralaterally coupled to a second side of a distal portion of the straight-line expansion strut of the second expansion column, and the distal stem of the second serial connecting strut is contralaterally coupled to a proximal portion of a first side of the straight-line expansion strut of the third expansion column.

51. The stent of claim 27, wherein in the second expansion column a longitudinal axes of the stair-step expansion strut has a first and a second longitudinal axis each being parallel to a longitudinal axis of the straight-line expansion strut.

52. An intra-luminal vascular stent in a non-expanded state with a longitudinal axis, comprising:
   a plurality of expansion strut pairs forming a first expansion column, each of an expansion strut pair including a first expansion strut, a second expansion strut and a joining strut coupling an end of the strut pair forming a cell slot;
   a plurality of expansion strut pairs forming a second expansion column, each of an expansion strut pair including a first expansion strut, a second expansion strut and a joining strut coupling an end of the strut pair forming a cell; and
   a plurality of serial connecting struts forming a first serial connecting strut column and including a first serial connecting strut, each of a first serial connecting strut having a proximal portion including a proximal stem and a proximal linear section, a distal portion with a distal stem and a distal linear section and a coupling intermediate portion, the first serial connecting strut column coupling the first expansion column to the second expansion column, the linear section of the first connecting strut proximal portion having a longitudinal axis that is parallel to the longitudinal axis of the stent.

53. The stent of claim 52, wherein at least one strut in a strut pair of the first expansion column has a stair-step configuration.

54. The stent of claim 53, wherein at least one strut in a strut pair of the second expansion column has a stair-step configuration.

55. The stent of claim 52, wherein at least one strut in a strut pair of the first expansion column having a straight-line configuration.

56. The stent of claim 52, wherein at least one strut in a strut pair of the second expansion column having a straight-line configuration.

57. The stent of claim 52, wherein at least one strut in a strut pair of the first expansion column having a stair-step configuration, and at least one strut in a strut pair of the second expansion column having a straight-line configuration.

58. The stent of claim 52, wherein at least one strut in a strut pair of the second expansion column having a stair-step configuration, and at least one strut in a strut pair of the first expansion column having a straight-line configuration.

59. The stent of claim 52, wherein the cell slots in the first expansion column are non-parallel to the cell slots in the second expansion column.

60. The stent of claim 52, wherein the cell slots of the first and second expansion columns are non-parallel to the longitudinal axis of the stent.

61. The stent of claim 52, wherein the first and second expansion columns and the first serial connecting strut column form a first set of stent cells.

* * * * *